Sept. 29, 1953 A. P. HOWARD Plant Pat. 1,218
ROSE PLANT
Filed Sept. 5, 1952
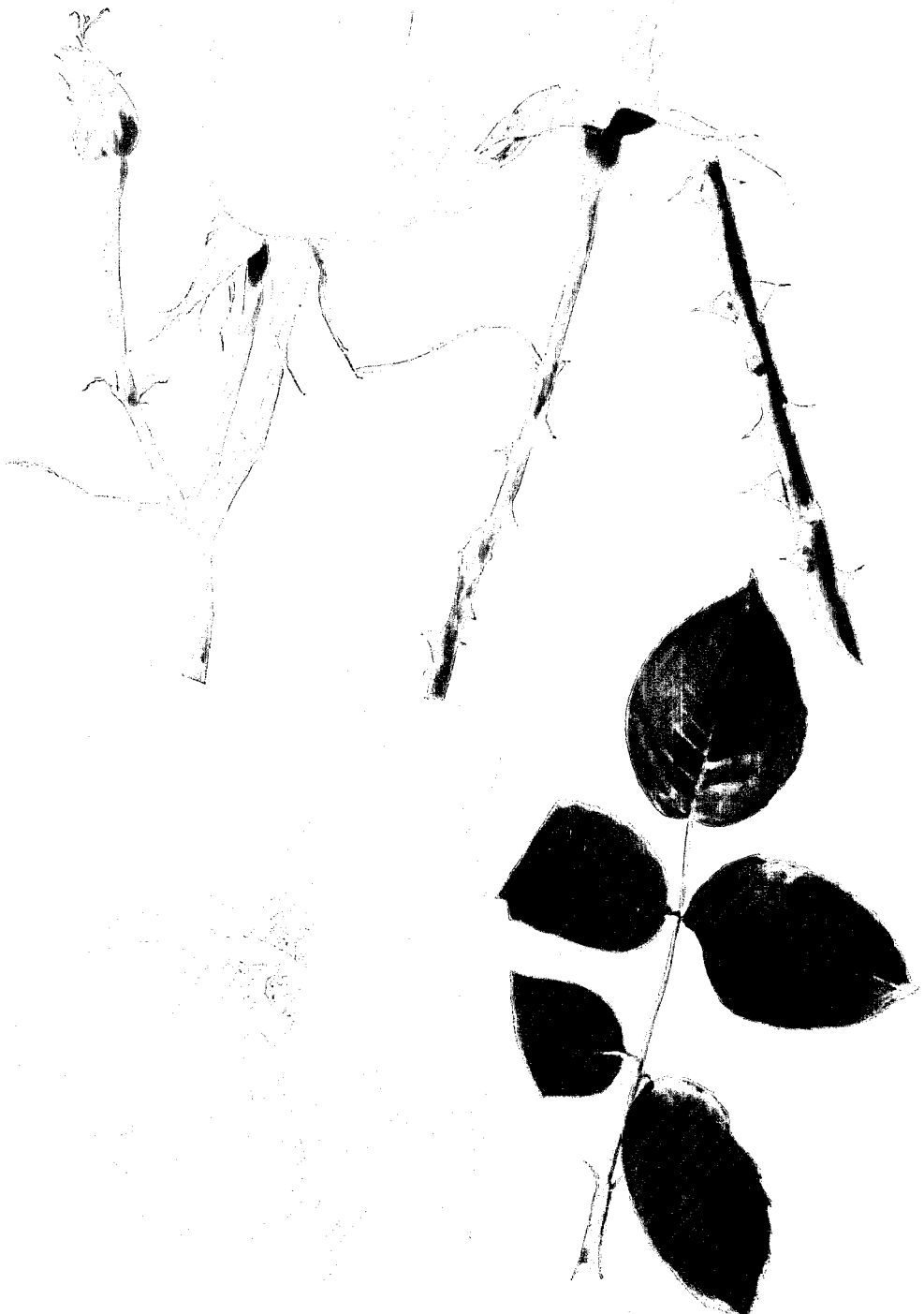
INVENTOR
Arthur Preston Howard
By Orville M. Kile
Plant Pat. Agt.

Patented Sept. 29, 1953

Plant Pat. 1,218

UNITED STATES PATENT OFFICE 1,218

ROSE PLANT

Arthur Preston Howard, Sierra Madre, Calif., assignor to Howard & Smith, Montebello, Calif.

Application September 5, 1952, Serial No. 308,092

1 Claim. (Cl. 47—61)

My present invention pertains to a new variety of hybrid tea rose plant in the light pink class, possessing a novel and desirable combination of characteristics. It originated as a seedling resulting from a cross made by me between the varieties Cl. Pink Dawn (unpatented) and The Doctor (unpatented), in an effort to strengthen the plant of The Doctor while retaining its highly desirable luminous pink bloom. This cross was made at our greenhouses in Montebello, California, and the resulting variety has been asexually reproduced by me at both Montebello and Puente, California, by budding.

The principal features of my new variety are the luminous, delicate, silvery pink color of its buds and flowers, the length of bud, the very free blooming habit, and the tall, strong, bunchy growth. It is taller, with heavier foliage and is much more floriferous and healthy than its parent, The Doctor. Compared with its parent, Cl. Pink Dawn, the new variety has longer buds, is a more profuse bloomer, its flowers are generally deeper in color when grown under similar conditions, and of course it does not have the climbing habit but grows more like the bush form of Pink Dawn.

The illustration accompanying this specification shows in approximately true colors, the buds and flowers of my new variety in various stages of opening and with portions of the flower stems. Alongside these are depicted a compound leaf and a portion of the lower stem showing the numerous large thorns.

In the following detailed description, color plate numbers refer to Ridgway's Color Standards and Nomenclature except in the case of the bud and flower description which refers to the British Horticultural Colour Chart.

*The plant*

Type or class: Hybrid tea.

Parentage: Cl. Pink Dawn × The Doctor.

Growth habit: Upright, strong grower, with no die-back. Grows to a height of 3 to 3½ feet.

Blooming habit: Very profuse bloomer, surpassing both Pink Dawn and The Doctor. Flowering season is continuous.

Disease resistance: This variety has shown less leaf spot than its parents and to date has been entirely free of mildew even when grown near infected plants.

Hardiness: Very hardy wherever tested.

Stems: Rigid, growing 1 to 2 feet in length. Color is Yellowish Oil Green (Pl. I). Matured stems shaded with Morocco Red (Pl. I).

Thorns: Many; irregularly spaced; outward-pointing; Morocco Red (Pl. I); up to $\frac{3}{16}$ inch in length.

Foliage:

*Type.*—Odd pinnate, usually with 5–7 leaflets.

*Quantity.*—Abundant.

*Shape.*—Ovate to oval, with rounded base and acuminate apex.

*Size.*—Terminal leaflet 1½ to 2 inches long; lateral leaflets slightly smaller.

*Color.*—Spinach Green (Pl. V) on upper surface; lighter underneath.

*Stipules.*—Adnate, with points ⅛ inch long.

Bud:

*Form.*—Long ovoid.

*Color.*—Crimson 22/2 (Hort. Colour Chart).

*Opening.*—Opens evenly.

*Size.*—Typical bud is approximately 1½ to 2¼ inches long just before opening. With slight variation due to soil and seasonal conditions, and grown under similar conditions, the buds are a half to three-quarters inch longer than those of Pink Dawn.

*Calyx.*—Small. Sepals mostly simple; long-pointed; $\frac{5}{16}$ to 1⅛ inches long and hooded over bud before opening.

*Peduncle.*—Strong; rigid; approximately 2 inches long.

Bloom: High-centered and loose, opening wide with petals somewhat reflexed.

*Size.*—Large. Usually 4 to 5 inches in diameter.

*Petalage.*—Usually about 24 to 28 petals.

*Color.*—Crimson 22/3 (Horticultural Colour Chart). There is a luminous, silvery quality about the color which is difficult to adequately describe or to show by means of water colors.

*Fragrance.*—Very pleasing tea rose fragrance.

*Longevity.*—Average.

Petals:

*Shape.*—Oribcular to ovate, ranging from outer to inner petals.

*Size.*—Approximately 1½ to 2½ inches by 2½ inches, for the larger outer petals.

*Texture.*—Very thick and of good substance.

*Aspect.*—Smooth.

*Persistence.*—Clinging.

Reproductive organs:

*Pistils.*—Few, bunched in center of flower. Styles very short; stigmas whitish.

*Stamens.*—Many, surrounding pistils. Filaments delicate pink, slender, short and uneven; anthers large, approximately Lemon Chrome to Buff Yellow (Pl. IV, Ridgway's); pollen sparse.

Having thus disclosed my invention, I claim:

The new and distinct variety of hybrid tea rose plant, substantially as herein disclosed, characterized particularly by the combination of its tall, strong, upright growth; its very free blooming habit; its long, slender bud; and the medium pink color of its flowers as described.

ARTHUR PRESTON HOWARD.

No references cited.